United States Patent [19]
Bebbington et al.

[11] Patent Number: 5,879,936
[45] Date of Patent: Mar. 9, 1999

[54] RECOMBINANT DNA METHODS, VECTORS AND HOST CELLS

[75] Inventors: Christopher Robert Bebbington, Windsor; Geoffrey Thomas Yarranton, Near Reading, both of United Kingdom

[73] Assignee: Aluguisse Holding A.G., Neuhausen Am Rheinfall, Switzerland

[21] Appl. No.: 898,165

[22] Filed: Jun. 12, 1992

Related U.S. Application Data

[63] Continuation of Ser. No. 460,154, Jan. 25, 1990, abandoned.

[30] Foreign Application Priority Data

Apr. 18, 1988 [GB] United Kingdom ............. 8809129

[51] Int. Cl.⁶ ..................................................... C12N 5/00
[52] U.S. Cl. .......................................... 435/325; 435/375
[58] Field of Search .................. 536/29.1; 485/69.1; 2/240.2, 240.27, 172.3

[56] References Cited

U.S. PATENT DOCUMENTS

| | | | |
|---|---|---|---|
| 4,656,134 | 4/1987 | Ringold | 435/91 |
| 5,122,464 | 6/1992 | Wilson et al. | 435/172.3 |

FOREIGN PATENT DOCUMENTS

| | | |
|---|---|---|
| 0255320 | 2/1988 | European Pat. Off. . |
| 0244677 | 11/1988 | European Pat. Off. . |
| 8704462 | 7/1987 | WIPO . |

OTHER PUBLICATIONS

Rodrued, Chapter 23 p. 369, in Review of Physiological Chemistry, 1977, Lange Medical Publication.
Foecking et al Gene 45:101, 1986.
Molecular Cloning: A Laboratory Manual pp.1645–1646, 1989.

*Primary Examiner*—Bruce R. Campell
*Attorney, Agent, or Firm*—Venable; John W. Schneller

[57] ABSTRACT

The present invention relates to vectors useful for transforming a lymphoid cell line to glutamine independence. The vectors comprise an active glutamine synthetase (GS) gene as well as a heterologous gene of interest to be expressed. The preferred embodiments encompass vectors wherein the heterologous gene is expressed from a relatively strong promoter and the GS gene is expressed from a relatively weak promoter. In one example, the heterologous gene is operatively linked to the hCMV-MIE promoter and the GS gene is operatively linked to the SV40 early region promoter.

9 Claims, 3 Drawing Sheets

RECOMBINANT DNA METHODS, VECTORS AND HOST CELLS

This application is a continuation application Ser. No. 07/460,154, filed Jan. 25th, 1990, abandoned.

BACKGROUND OF THE INVENTION

The present invention relates to methods for improving the usefulness of lymphoid cell lines as host cells for the production of proteins by recombinant DNA technology. The present invention also relates to vectors for use in such methods and to host cells produced by such methods.

Lymphoid cell lines are at present being appraised for use as host cells in the production by recombinant DNA technology of immunoglobulin molecules, related hybrid or chimeric proteins (Ig-type molecules), or other recombinant proteins. Since the lymphoid cells include myeloma cells which are of the same general type as the B cells which produce Ig molecules in vivo, it is envisaged that they will naturally possess the intracellular mechanisms necessary to allow proper assembly and secretion of Ig-type molecules. Such lymphoid cell lines may also be of use in the production by recombinant DNA technology of non-Ig-type molecules.

It is known that many lymphoid cell lines, such as myeloma cell lines and T cell lymphomas, cannot be grown in vitro on media lacking in glutamine. It has been suggested that it would be useful to be able to transform lymphoid cell lines to glutamine independence, since this may provide an advantageous method for selecting transformed cell lines.

It has been conjectured that such a cell line could be transformed to glutamine independence by incorporating therein a gene coding for glutamine synthetase (GS). Such a suggestion is made in EP-A-0 256 055 (Celltech). However, it has subsequently been found that hybridoma cell lines can generate spontaneous variants able to grow in a glutamine-free medium at such a high frequency that the identification of transfectants is difficult or impossible. For myeloma cell lines, transfection with a GS gene and growth of the transformed cells in a glutamine-free medium does not result in significant survival rates.

It is therefore an object of the present invention to provide a method for transforming lymphoid cell lines to glutamine independence.

SUMMARY OF THE INVENTION

According to the present invention, there is provided a method for transforming a lymphoid cell line to glutamine independence which comprises:
 transforming the lymphoid cell line with a vector containing an active glutamine synthetase (GS) gene;
 growing the transformed cell line on a medium containing glutamine; and
 continuing the growth of the transformed cell line on a medium in which the glutamine is progressively depleted or on a medium lacking glutamine.

Preferably, the lymphoid cell line is a myeloma cell line.

Preferably, the glutamine-depleted or glutamine-free medium contains asparagine. Alternatively the medium contains another nutrient which enables the transformed cell line to survive on a glutamine free medium. This other nutrient may be an ammonia donor, such as ammonium chloride.

It has surprisingly been found that if the transformed lymphoid cell line is not firstly grown on a glutamine-containing medium, it is not possible to obtain the growth of any cell line, whether or not it has been transformed by the vector. By use of the method of the present invention, it is possible to select for lymphoid cell lines which have been transformed by the vector.

Alternatively, the lymphoid cell line may be transformed with a vector containing both an active GS gene and a gene encoding another selectable marker, such as a gpt gene, or cotransformed with separate vectors encoding GS and the selectable marker respectively. Transformed host cells can then be selected using the selectable marker prior to depletion of glutamine in the medium.

The advantage of this method is that it enables selection for vector maintenance to be achieved without the use of a toxic drug. Host cells in which the vector is eliminated will not be able to survive in a glutamine-free medium.

A further advantage of this method is that it enables selection for gene amplification to be carried out without the risk of amplification of the host cell's endogenous GS genes.

Preferably the glutamine in the medium is progressively depleted by dilution with a medium containing aspargine but lacking glutamine.

Preferably, the vector used to transform the lymphoid cell line also contains an active gene coding for a protein heterologous to the lymphoid cell line. Alternatively, the lymphoid cell line may be co-transformed with a separate vector containing the active gene coding for the heterologous protein.

The heterologous protein may be one which is expressed as a single chain (although it may be cleaved after expression into a multichain protein). Examples of such single chain expression products are tissue plasminogen activator (tPA), human growth hormone (hGH) or tissue inhibitor of metalloproteinase (TIMP).

Preferably, however, the heterologous protein is an Ig-type molecule. Such molecules require the separate expression of two peptide chains which are subsequently assembled to form the complete molecule. Thus, the cell line will need to be transformed with active genes which encode separately a heavy chain (or heavy chain analog) and a light chain (or light chain analog).

Preferably, the genes encoding the heavy and light chains are both present on the same vector as the GS gene. Alternatively, the vector containing the GS gene may have one of the heavy or light chain genes thereon, the other gene being on a separate vector. In a second alternative, the light and heavy chain genes are not present on the vector containing the GS gene but are present on the same or different vectors.

The expression of such heterologous proteins may be substantially increased by subsequent selection for GS gene amplification, for instance using methionine sulphoximine (MSX) as the selection agent.

It is preferred that the GS gene comprises a relatively weak promoter and that the gene (or genes) encoding the heterologous protein comprises a relatively strong promoter so that in the transformed cell lines, protein synthesis is directed preferentially to the production of the heterologous protein or peptide rather than to the production of GS. Moreover, a lower concentration of selection agent, such as MSX, will be required to select for gene amplification if the GS gene is controlled by a weak, rather than a strong, promoter.

It is also conjectured that use of a weak promoter may enable the selection of transformed cell lines wherein the GS gene has been inserted at a particularly advantageous location in the genome. This will ensure that both the GS gene and any heterologous genes will be transcribed efficiently.

It has been found that, in the preferred case, where all the genes are present on the same vector, it is necessary to design the vector carefully in order to achieve proper expression of the genes.

Thus, according to a second aspect of the present invention, there is provided a vector for transforming a lymphoid cell line to glutamine independence and to enable it to produce a heterologous protein, the vector comprising a GS gene and a gene encoding the heterologous protein, wherein the vector is arranged such that expression of the GS gene is not hindered by transcriptional interference from the promoter/enhancer transcribing the sequence coding for the heterologous protein to such an extent that glutamine-independent colonies cannot be produced.

Preferably, the genes on the vector are arranged in such orientations and with such promoters as substantially to prevent transcriptional interference. For instance, the GS gene may contain a relatively weak promoter, the gene encoding the heterologous protein may contain a relatively strong promoter, and the promoter of the GS gene may be located upstream of or may direct expression in the opposite direction to that of the gene encoding the heterologous protein.

It has surprisingly been found that if the vector arrangement set out above is adopted, the GS gene is expressed in sufficient quantity to enable selection to be made and the heterologous protein is expressed more efficiently than with other vector arrangements.

It has been observed that other vector arrangements, for instance using different promoters or a different ordering or orientation of the genes, can lead to a much reduced or even non-existent level of GS or heterologous protein production. It is conjectured (although the applicants do not wish to be limited to this theory) that if a gene containing a strong promoter is located upstream of a GS gene having a weaker promoter, the transcription of the upstream gene will run through into the downstream gene, thus producing occlusion of the downstream promoter. Since the frequency of transformed colonies is critically dependent on the level of GS gene expression, such promoter occlusion dramatically reduces the frequency with which transfectants are recovered.

A preferred combination for the weak and strong promoters is the SV40 early region and the hCMV-MIE promoters. (hCMV-MIE=human cytomegalovirus major immediate early gene). However, other suitable promoter combinations will be readily apparent to those skilled in the art.

A particularly preferred embodiment of the vector of the present invention comprises a GS gene having a weak promoter having downstream therefrom a heavy chain-like gene having a strong promoter, there being on the vector a light chain-like gene having a strong promoter oriented in the opposite direction to the promoters of the GS and heavy chain-like genes.

Alternatively, promoter occlusion may be prevented by use of transcription terminator signals between the genes.

In another alternative, the genes may be arranged with a unique restriction site between them. This site can then be used to linearise the vector before it is incorporated into the host cell. This will ensure that in the transformed host cell no promoter occlusion can take place.

It will be appreciated that if the vector contains more than one gene encoding a heterologous protein, it will be necessary to ensure that none of the genes in the vector can promote transcriptional interference. For instance, if the vector contains a GS gene, a heavy chain gene and a light chain gene, it is preferred that either all three genes are transcribed in the same direction and that the GS gene is upstream of the other two genes or that the GS gene and one of the other genes are transcribed in the same direction, the GS gene is upstream of the first other gene, and the second other gene is transcribed in the other direction, and the promoter of the second other gene is located adjacent the promoter of the GS gene.

The vector may comprise a viral vector, such as lambda phage, or a plasmid vector, for instance based on the well known pBR322 plasmid. However, any other of the vectors well known in the art may be adapted by use of conventional recombinant DNA technology for use in the present invention.

The present invention also includes host cells produced by the method of the invention or containing vectors according to the invention.

In particular, the present invention includes a lymphoid cell line which has been cotransformed with a vector containing a GS gene and a vector containing a gene encoding a heterologous protein, the vectors being arranged to ensure that the GS gene is not hindered by transcriptional interference to such an extent that glutamine-independent colonies cannot be produced.

BRIEF DESCRIPTION OF THE DRAWINGS

The present invention is described below by way of example only with reference to the accompanying drawings in which.

Figure 1:
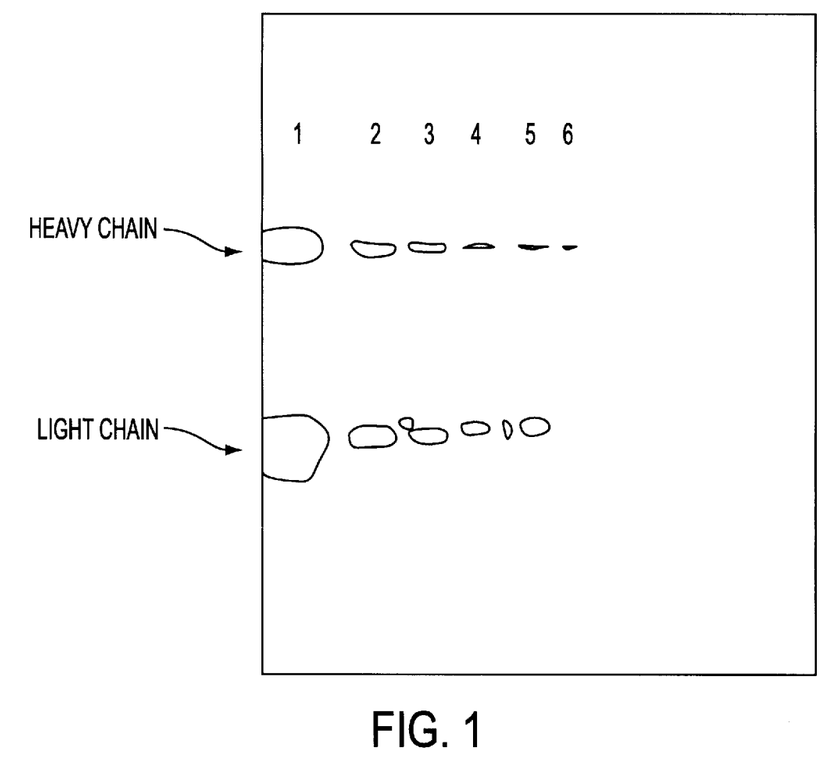
FIG. 1 shows an analysis of proteins secreted by NSO cells transfected with plasmid pAB2GS by Western blotting in which 25 μl of culture supernatant or control tissue culture medium was run on a 10% SDS reducing polyacrylamide gel, blotted onto nitro-cellulose and probed with antisera recognising human Ig chains and then with $^{125}$I-labelled protein A.

In FIG. 1 of the drawings lane 1 shows purified chimeric B72.3 antibody to show the position of Ig light and heavy chains, lanes 2 to 5 show culture supernatants from four different transfected clones, and lane 6 shows culture medium as a negative control.

Figure 2:
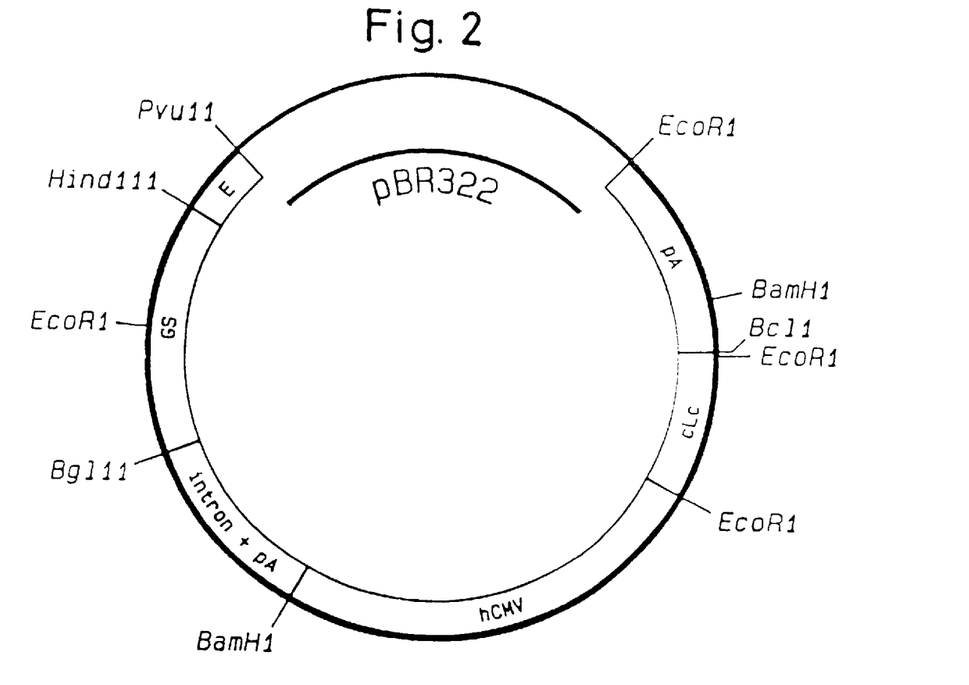
FIG. 2 shows the structure of plasmid pSV2GScLc.

In FIG. 2, E is the SV40 early region promoter, GS is a GS cDNA coding sequence, intron+PA is the small t-intron and the early region polyadenylation signal of SV40, hCMV is the hCMV-MIE promoter-enhancer, cLc is the coding sequence for the chimeric L-chain of a humanised antibody known as B72.3, and pA is the SV40 early polyadenylation signal.

Figure 3:
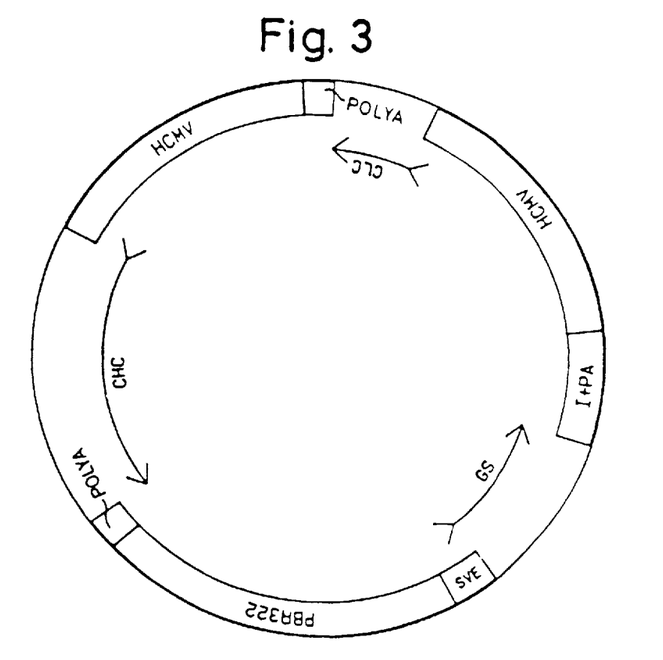
FIG. 3 shows the structure of plasmid pST6.

In FIG. 3, hCMV is the hCMV-MIE promoter enhancer (2.1 kb) fragment. CHC is the chimeric heavy chain coding sequence of the B72.3 antibody. CLC is the chimeric light chain coding sequence of the B72.3 antibody. Poly A contains the SV40 early polyadenylation signal. I+PA contains the small t intron of SV40 and the early region polyadenylation signal. SVE is the SV40 early promoter. A bacterial plasmid origin of replication and ampicillin resistance gene are provided by pBR322.

Figure 4:
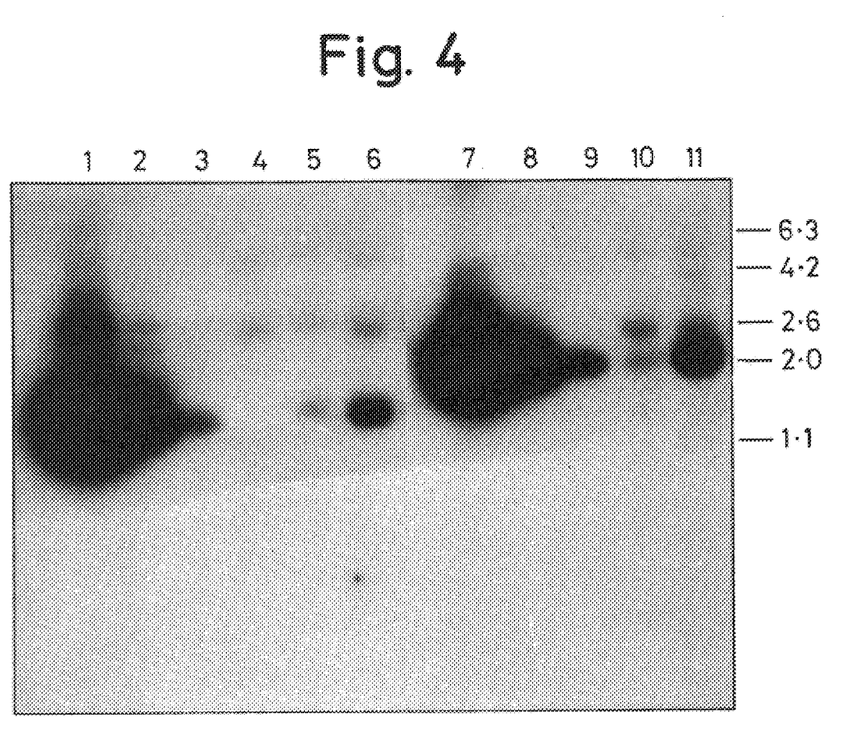
FIG. 4 shows a Southern blot analysis of genomic DNA from cell lines SV2GSNSO and CMGSNSO.

FIG. 4 shows a copy number analysis of GS-vectors in NSO cells before and after selection with MSX. DNA samples were digested with BglI and BglII, electrophoresed on a 1% agarose gel, transferred to nitrocellulose and probed with the 0.5 kb 5' Pst1 DNA fragment of pGSC45 [11] isolated from a GS cDNA.

DNA samples are as follows:

| | |
|---|---|
| Lane 1 | plasmid pSV2GS equivalent to 100 copies/cell |
| Lane 2 | plasmid pSV2GS equivalent to 10 copies/cell |
| Lane 3 | plasmid pSV2GS equivalent to 1 copy/cell |
| Lane 4 | 10 μg NSO genomic DNA |
| Lane 5 | 10 μg SV2GSNSO genomic DNA |
| Lane 6 | 10 μg SV2GSNSO (100 μM MSX resistant) genomic DNA |
| Lane 7 | plasmid pCMGS equivalent to 100 copies/cell |
| Lane 8 | plasmid pCMGS equivalent to 10 copies/cell |
| Lane 9 | plasmid pCMGS equivalent to 1 copy/cell |
| Lane 10 | 10 μg CMGSNSO genomic DNA |
| Lane 11 | 10 μg CMGSNSO (100 μM MSX resistant) genomic DNA |
| m.w. | λ phage DNA digested with Cla1; molecular weight markers. |

DETAILED DESCRIPTION OF THE INVENTION

A list of references is given at the end of the description. In the following, the references are indicated by numbers enclosed in square brackets.

Vectors

In the following Examples, for comparative purposes, two plasmids described in EP-A-0 256 055 were used. These are plasmids pSVLGS1 and pSV2GS. Plasmid pSVLGS1 contains a GS minigene, containing cDNA and genomic DNA sequences, under the control of a SV40 late region promoter. Plasmid pSV2GS contains a cDNA sequence encoding GS under the control of a SV40 early region promoter.

A vector pSV2BamGS was produced by converting the unique PvuII site in pSV2GS to a BamHI site by the addition of a synthetic oligonucleotide linker.

By use of synthetic oligonucleotide linkers, the major immediate early gene promoter, enhancer and complete 5'-untranslated sequence from human cytomegalovirus (hCMV-MIE) (the Pst-1m fragment [1] together with a synthetic oligonucleotide to recreate the remaining 5' untranslated sequence) was inserted between the NcoI sites of pSV2GS such that the hCMV-MIE promoter directs expression of the GS coding sequence. The resulting plasmid was labelled pCMGS.

Plasmid pSV2BamGS was digested with BamHI to give a 2.1 kb fragment containing the transcription cassette.

For convenient construction of other expression plasmids, a basic vector pEE6 was used. Plasmid pEE6 contains the XmnI to BclI fragment of plasmid pCT54 [2] with the polylinker of plasmid pSP64 [3] inserted between its HindIII and EcoRI sites but with the BamHI and SAlI sites removed from the polylinker. The BclI to BamHI fragment is a 237 bp SV40 early gene polyadenylation signal (SV40 nucleotides 2770–2533). The BamHI to BglI fragment is derived from plasmid pBR322 [4] (nucleotides 275–2422) but with an additional deletion between the SalI and AvaI sites (nucleotides 651–1425) following addition of a SalI linker to the AvaI site. The sequence from the BglI site to the XmnI site is from the β-lactamase gene of plasmid pSP64 [3].

Plasmid pEE6gpt contains the transcription unit encoding xanthine-guanine phosphoribosyl transferase (gpt) from plasmid pSV2gpt [5] cloned into plasmid pEE6 as a BamHI fragment by the addition of a BamHI linker to the single PvuII site of plasmid pSV2gpt.

By similar means, a derivative of plasmid pCMGS containing the transcription cassette for the xanthine-guanine phosphoribosyl transferase (gpt) gene from pEE6gpt was produced. The plasmid thus produced was labelled pCMGS-gpt.

Plasmid pEE6hCMV contains the hCMV-MIE promoter-enhancer and complete 5' untranslated sequence inserted by means of oligonucleotide linkers into the HindIII site of plasmid pEE6.

Plasmid pEE6hCMVBglII is a derivative of pEE6hCMV in which the HindIII site upstream of the hCMV enhancer has been converted to a BglII site by blunt-ending and addition of a synthetic oligonucleotide linker.

Plasmid pEE6HCLCBg is a vector derived from pEE6hCMV containing a coding sequence for a mouse-human chimeric Ig light chain from the B72.3 antibody [6] inserted into the EcoRI site of pEE6hCMV such that the light chain is under the control of the hCMV-MIE promoter-enhancer. (The upstream HindIII site has also been converted to a BglII site by standard methods.) The 2.1 kb BamHI fragment from pSV2BamGS was inserted into pEE6HCLCBg to produce a plasmid pcLc2GS in which the Ig light chain and GS genes are transcribed in the same orientation with the GS gene downstream of the light chain gene.

pEE6HCHHCL is a vector which contains sequences coding for both the heavy and light chains of the chimeric B72.3 antibody [6] under the control of hCMV-MIE promoter enhancers. The 2.1 kb BamHI fragment from pSV2BamGS was inserted into pEE6HCHHCL to produce a plasmid pAb2GS in which the heavy and light chain genes and the GS gene are all transcribed in the same orientation in the order heavy chain, light chain, GS.

A 3.1 kb BglII-BamHI fragment from pEE6HcLcBg was inserted into the BamHI site of pSV2GS to produce a plasmid pSV2GScLc in which the chimeric light chain gene and the GS gene are transcribed in the same orientation with the GS gene upstream of the light chain gene.

Similarly, the 3.1 kb BglII-BamHI fragment of PEE6HCLCBg was inserted into the BamHI site of pCMGS to produce a plasmid pCMGS.CLC in which both genes are again in the same orientation.

pEE6CHCBg is a plasmid containing the heavy chain gene of chimeric B72.3 antibody [6] under the control of the hCMV-MIE promoter-enhancer and SV40 polyadenylation signal. The hCMV-MIE chain termination unit was excised from the plasmid as a 4.7 kb partial HindIII-BamHI fragment and inserted, by means of a HindIII-BamHI oligo-nucleotide adaptor, at the single BamHI site of pSV2GScLc to form pSV2GScLccHc. The BamHI site upstream of the hCMV-MIE-cH chain transcription unit in pSV2GScLccHc was then removed by partial BamHI digestion, filling in with DNA polymerase I and religating to form pST6.

A gene coding for a novel fibrinolytic enzyme of 90 kD molecular weight was isolated as a 2.8 kb HindIII to BglII fragment. This was then inserted between the HindIII and BclI sites of the expression plasmid pEE6hCMVBglII in the appropriate orientation such that the hCMV promoter directed transcription of the inserted gene. An SV40 Early-GS transcription unit was excised as a BamHI fragment from pSV2GS and inserted into the BglII site at the 5' end of the hCMV sequence in pEE6hCMVBglII, in the appropriate orientation such that transcription from the hCMV promoter and the SV40 early promoter is in the same direction. This formed the plasmid pEE690KGS.

Cell Lines

In the Examples, the following cell lines were used: NSO and P3-X63Ag8.653, which are non-producing variants of the mouse P3 mouse plasmacytoma line; Sp2/0, which is a non-producing mouse hybridoma cell line; and YB2/0, which is a non-producing rat hybridoma cell line.

Media

All cells were grown in either non-selective medium, Dulbecco's Minimum Essential Medium (DMEM) containing 2 mM glutamine, 100 µM non-essential amino acids, 10% foetal calf serum and streptomycin/penicillin, or in glutamine-free DMEM (G-DMEM) containing 500 µm each of glutamate and asparagine, 30 µM each of adenosine, guanosine, cytidine and uridine, 10 µM thymidine, 100 µM non-essential amino acids, 10% dialysed foetal calf serum and streptomycin/penicillin, or in derivatives of G-DMEM lacking various of these additives.

Alternatively, cells were cultured in gpt-selective media, made using the following filter-sterilised stock solutions: 1) 50× each of hypoxanthine and thymidine; 2) 50× xanthine (12.5 mg/ml in 0.2M NaOH); 3) mycophenolic acid (MPA, 250 µg/ml in 0.1M NaOH); and 4) 1M HCl. gpt-selective medium is made by mixing 93 ml of non-selective medium (described above), 2 ml solution 1), 2 ml solution 3), and 0.6 ml solution 4). 2× gpt is made by mixing 86 ml of non-selective medium with twice the above quantities of solutions 1) to 4).

Linearisation of Plasmids

In order to introduce them into cells all plasmids were linearised by digestion with an appropriate restriction enzyme which cuts at a single site in the plasmid and hence does not interfere with transcription of the relevant genes in mammalian cells. Typically 40 µg of circular plasmid was digested in a volume of 400 µl restriction buffer. The enzymes used for linearisation of the plasmids are shown in Table 1.

TABLE 1

Enzymes used for Linearisation of Plasmid

| Plasmid | Restriction Enzyme |
|---|---|
| pSVLGS.1 | PvuI |
| pSV2.GS | PvuI |
| pSV2.Bam GS | PvuI |
| pCMGS | PvuI |
| pCMGS.gpt | PvuI |
| PEE6.gpt | SalI |
| pcLc2GS | SalI |
| pAb2GS | SalI |
| pSV2.GScLc | TthIII |
| pCMGS.cLc | TthIII |
| pST6 | BamHI |
| pEE690KGS | SalI |

Electroporation of Cells

Cells were harvested while growing exponentially, washed once in phosphate-buffered saline (PBS) by centrifugation at 1200 rpm in a bench centrifuge and resuspended at a density of $10^7$ cells/ml in fresh ice cold PBS. One ml of cell suspension was added to the digested plasmid DNA (0.4 ml in restriction buffer) and incubated on ice for 5–10 minutes. The cell-DNA mixture was then subjected to 2 pulses of 2000 volts between aluminium electrodes spaced approximately 1 cm apart using a conventional electroporation apparatus having a capacitance of 14 µF. Cells were then returned to ice for 5–10 minutes, resuspended in non-selective growth medium (DMEM) and distributed among 24-well culture trays. Selective medium (G-DMEM) was added subsequently as described below.

EXAMPLE 1

Preliminary experiments indicated that the plasmid pSV-LGS1 which has been used successfully as a selectable marker in CHO-K1 cells (see EP-A-0 256 055) could not be introduced into NSO cells to confer glutamine independent growth at efficient rates. Only a very low frequency of approximately 6 transfected colonies per $10^7$ cells was obtained. This should be compared with the transfection frequencies in excess of $1/10^4$ transfected cells which are obtained using the xanthine-guanine phosphoribosyl transferase (gpt) selectable marker gene from pEE6gpt and selecting for resistance to mycophenolic acid in medium containing xanthine, hypoxanthine and thymidine. Preliminary experiments using pCMGS, in which the GS cDNA is expressed from the hCMV-MIE promoter yielded a much higher frequency of glutamine-independent colonies and pSV2GS, which utilises the SV40 early region promoter, yielded an intermediate transfection frequency.

In order to establish a suitable protocol for consistent use in selection, 20 µg linearised pCMGS and 20 µg of linearised pEE6gpt were mixed and introduced together into $10^7$ NSO cells. A separate aliquot of $10^7$ cells was "mock" transfected by electroporation without added DNA.

The cells were plated in 24-well plates as described above in 0.5 ml non-selective medium (DMEM) and 24 hours later, selection was applied to wells of the "mock" and DNA transfected plates as follows:

A added 1 ml G-DMEM and left for 7 days before examining plates.

B added 1 ml G-DMEM on day 1, aspirated on day 2 and replaced with fresh G-DMEM.

C added 1 ml G-DMEM containing 200 µM glutamine on day 1, left for 2 more days then aspirated and replaced with G-DMEM.

D left on day 1 and added 1 ml G-DMEM on day 2. On day 3, medium was aspirated and replaced with fresh G-DMEM.

E left on day 1 and aspirated on day 2 and replaced with 1 ml G-DMEM. The wells were aspirated again on day 4 and replaced with fresh G-DMEM.

F mycophenolic acid selection: added 0.5 ml gpt-selective medium and on day 2 added 0.5 ml of 2× gpt-selective medium.

The number of surviving colonies in each of at least 3 wells for each selective protocol was scored 7–10 days after transfection and the mean results are shown in Table 2.

TABLE 2

| Selective Protocol | Mean No. colonies/$10^6$ cells plated | |
|---|---|---|
| | MOCK | pCMGS + pEE6gpt |
| A | 0 | 130 |
| B | 0 | 3 |
| C | 0 | 72 |
| D | 0 | 8 |
| E | 0 | 8 |
| F | 0 | 115 |

From these results it appears that protocol A (addition of 1 ml G-DMEM one day after transfection) provides the highest survival of transfected colonies and the frequency obtained when selecting for the introduced GS gene is equal to the transfection efficiency measured by selection for the gpt gene (Protocol F). Addition of a small amount of glutamine and aspiration after 2 more days, to replace with G-DMEM alone, (protocol C) provides the next highest frequency of glutamine independent colonies. However, removing the medium by aspiration and hence complete removal of glutamine (protocols B, D and E) severely reduces the number of surviving colonies. It can thus be seen that progressive depletion of glutamine in the medium leads to an enhanced selection procedure. Therefore protocol A was used in all subsequent experiments.

A strong promoter such as the hCMV-MIE promoter is likely to provide a high level of GS expression and hence will require a high level of MSX to select for gene amplification.

In order to determine whether a weaker promoter than the hCMV-MIE promoter-enhancer can be used to express a GS cDNA to obtain glutamine-independent transformants, 40 μg linearised pSV2BamGS, which uses the SV40 Early region promoter for GS expression, was introduced into NSO cells and selected using Protocol A. The results are shown in Table 3.

TABLE 3

| DNA Transfected | Selection Protocol | Mean No. Colonies/$10^6$ Cells |
|---|---|---|
| 20 μg pCMGS | A | 100 |
| 20 μg pEE6gpt | F | 40 |
| 40 μg pSV2BamGS | A | 20 |
| "Mock" | A | 0 |

Thus it appears that the GS-transcription unit in pSV2BamGS can indeed be used as a selectable marker in NSO cells but confers glutamine independence at a lower frequency than does pCMGS.

In order to test whether the GS gene in pSV2BamGS can be used as a selectable marker for the introduction of heterologous DNA into NSO cells, three different plasmids were constructed which contain different non-selectable linked genes all under the control of the hCMV MIE promoter-enhancer. These are pcLc2GS, which contains the chimeric B72.3 immunoglobulin light-chain gene; PTIMPGS, which contains the gene for tissue inhibitor of metalloproteinase (TIMP); and pAb2GS which contains both heavy and light chain genes for the chimeric B72.3 monoclonal antibody. Each was introduced into NSO cells as a linear plasmid using 40 μg of pcLc2GS and PTIMPGS and 80 μg of pAb2GS per $10^7$ cells transfected. The transfection frequency was $4/10^7$ cells for pAb2GS and no colonies were obtained with either of the other two plasmids. The 4 colonies obtained from transfection with pAb2GS were grown in bulk culture and spent culture supernatant analysed by Western blotting using anti-heavy and anti-light chain antibodies. The result is shown in FIG. 1. It is clear that all 4 clones secrete both heavy and light chains but at very low level (undetectable by enzyme-linked immunosorbent assay). Thus the GS-transcription unit from pSV2BamGS can be used as a selectable marker to introduce heterologous genes into NSO cells but the presence of such genes in these particular plasmid constructions seems to reduce substantially the frequency with which transfected colonies can be isolated. It is likely that this is due to an interference between the various transcription units on the plasmid. Hence only those few colonies in which the genes upstream of the GS-transcription unit are for some reason exceptionally poorly expressed, can yield sufficient GS for survival.

In order to test whether the position of genes on the vector was indeed responsible for the dramatic reduction in frequency of transformation to glutamine-independent growth, plasmids were constructed in which the GS gene transcription is upstream of a cL chain gene instead of downstream as in the previous experiments. The two plasmids chosen were pCMGScLc and pSV2GScLc, in which the GS gene is under the control of the hCMV-MIE promoter. These plasmids were introduced into NSO cells and transfectants selected using Protocol A. The number of colonies obtained is shown in Table 4.

TABLE 4

| Plasmid | No. Colonies/$10^6$ cells |
|---|---|
| pCMGS | 250 |
| pCMGS.cLc | 300 |
| pSV2.GS | 18 |
| pSV2GS.cLc | 9 |
| pcLc2GS | 0 |

These results show that whereas pcLc2GS, in which the GS gene is downstream of the cLc gene, yields no glutamine-independent colonies, the equivalent plasmid, pSV2GScLc, which has the gene order reversed, with the GS gene upstream, yields a transformation frequency comparable to that obtained using the GS gene alone (pSV2GS).

This study suggests that any interference of the SV40 early promoter used to express GS is reduced by placing the strong hCMV-MIE promoter downstream. The results in Table 4 also show no significant difference in the transformation efficiency obtained with pCMGScLc compared with pCMGS, again indicating no interference with GS expression.

The transfectants obtained with plasmids pCMGScLc and pSV2GscLc were assayed for cL chain secretion using an ELISA assay for human kappa chain antigen activity in spent culture medium. All culture wells from the pCMGScLc transfection, each containing many transfected colonies, did indeed secrete significant amounts of antigen. Seven out of ten wells from the pSV2GScLc transfection, again containing multiple colonies, also secreted detectable levels of light chain.

This is marked contrast to the results obtained with plasmids in which the GS gene is downstream of the second gene controlled by the hCMV-MIE promoter and demonstrates that the GS gene can be used as an effective selectable marker in this cell type, provided that the plasmid is appropriately designed.

pSV2GS is a particularly suitable vector into which heterologous genes may be inserted and pSV2GScLc is shown in FIG. 2.

In order to test which of the additives present in G-DMEM is essential for the growth of GS transfectants, pooled transfected cells containing the plasmid pCMGScLc were distributed among wells of a 24 well tissue culture tray in DMEM with 10% dialysed foetal calf serum and containing all possible combinations of the following additives at the concentrations present in G-DMEM: a) non-essential amino acids; b) glutamate; c) asparagine; d) adenosine, guanosine, cytidine, uridine and thymidine. Growth was scored after four days and the results are shown in Table 5.

TABLE 5

| Medium Additions | Growth |
|---|---|
| None | − |
| abcd | ++ |
| abc | ++ |
| abd | ++ |
| ab | ++ |
| ac | ++ |
| ad | ++ |
| a | ++ |

TABLE 5-continued

| Medium Additions | Growth |
|---|---|
| b | − |
| bc | ++ |
| bd | − |
| bcd | ++ |
| c | ++ |
| cd | ++ |
| d | − |
| bx4 | − |

From this it is clear that 500 μM asparagine is sufficient to sustain growth of GS transfectants in the absence of any other of the additives in G-DMEM. Surprisingly, glutamate, the substrate for GS, will not sustain growth of these cells, even when the concentration is raised to 2 mM. Non-essential amino acids can be used instead of 500 μM asparagine to support growth of these transfectants, but as this additive contains 100 μM asparagine, it is possible that this concentration of asparagine alone is sufficient to support growth.

It is clear that the NSO cell line must contain insufficient active GS-enzyme to permit growth in the glutamine-free medium used here and that a plasmid such as pCMGS yields sufficient GS when expressed in these cells to allow glutamine independent growth. Clones expressing a GS gene under the control of a weaker promoter, such as the SV40 Early promoter, on average express less GS enzyme and only a proportion of transfectants can survive in the glutamine-free medium.

In order to test whether GS-vectors can be used to confer glutamine-independent growth on other lymphoid cell lines, the growth of three additional cell lines in glutamine-free media was investigated. P3-X63Ag8.653 (a mouse myeloma) was also found to be completely incapable of growth in G-DMEM. When $10^7$ cells were plated out in a 24-well plate and selected using Protocol A, no glutamine independent variants were isolated. In contrast the non-secreting mouse hybridoma SP2/0 generated variants able to grow in G-DMEM at a frequency of approximately $1/10^5$ cells plated. Since the transfection frequency in this cell line (eg using pEE6gpt) is also about $1/10^5$ cells plated, this cell line is unsuitable as a host for GS selection using this protocol.

The rat non-secreting hybridoma YB2/0 also yielded glutamine-independent variants at an even higher frequency, estimated at $1/10^2$, making this cell line unsuitable for use with the GS-selection protocol developed above. A glutamine-independent variant of YB2/0 was cloned and a clonal cell line, designated YOG-F10, was grown in bulk culture and stored as frozen stocks in liquid nitrogen. A similar cloned cell line, a glutamine-independent variant of SP2/0, termed SPG2-E4 was also stored in liquid nitrogen. Such cell lines will be suitable for the introduction of vectors containing GS genes by methods described in EP-A-0 256 055.

In order to test whether selection for glutamine-independent transformants can be used to introduce plasmid vectors into P3-X63Ag8.653 cells, 40 μg linear pCMGSgpt (a vector containing both the GS-transcription unit from pCMGS and the gpt gene from pEE6gpt) was introduced by electroporation into $10^7$ P3-X63Ag8.653 cells. The results are shown in Table 6.

TABLE 6

Transfection of P3-X63-Ag8.653

| PLASMID | SELECTION PROTOCOL | NO. COLONIES/$10^6$ CELLS |
|---|---|---|
| pCMGS.gpt | A | 120 |
|  | F | 24 |
| "Mock" | A | 0 |
|  | F | 0 |

Thus the hCMV-GS transcription unit and selection Protocol A chosen for NSO cells can be used to obtain glutamine-independent P3-X63Ag8.653 at a frequency which is at least as great (possibly higher) than obtained using gpt selection. It should be noted that interference ("promoter occlusion") between the two transcription units could account for the lower frequency at which gpt-selected colonies arise.

The myeloma cell lines NSO and P3-X63Ag8.653 have been successfully transformed to glutamine independent growth by transfection with GS-expression plasmids. In contrast, two lines, YB2/0 and SP2/0 generate glutamine-independent variants at too high a frequency for GS-plasmids to be used in this way as selectable markers in these cells. It is also demonstrated here that a GS-expression plasmid such as pSV2GS can be used to introduce non-selected genes such as the genes encoding the B72.3 chimeric antibody into NSO cells. The arrangement of genes on the plasmid have marked effects on the expression levels attained from these genes and it will be important to take this into account in the design of optimal expression vectors. Transcription from a strong promoter such as the hCMV-MIE promoter-enhancer should not be permitted to proceed towards a gene expressed from a weaker promoter, such as the SV40 Early promoter unless the two genes are separated, e.g. by a transcription termination signal.

EXAMPLE 2

In order to confirm that the GS-transcription units in plasmids such as pCMGS and pSV2BamGS can act as amplifiable selectable markers in a myeloma cell line, the copy number of vector DNA introduced into NSO cells by electroporation was analysed before and after selection for GS-gene amplification using methionine sulphoximine (MSX).

NSO cells were transfected with pSV2BamGS or pGMGS as described above and pools of transfected colonies (at least 20 colonies from each transfection) were expanded in culture to form cell lines SV2GSNSO and CMGSNSO. These two cell pools were then distributed among the wells of a 24-well cell culture tray at a cell density of approximately $10^5$ cells/well in G-DMEM medium. MSX was added to the wells to final concentrations ranging between 20 and 80 μM. After incubation for several days, extensive cell death was observed in all wells and, after 2–3 weeks, MSX-resistant colonies were visible at concentrations of-MSX up to 60 μM for the SV2GSNSO cell line and up to 80 μM for the CMGSNSO cell line. Cells isolated at these concentrations of MSX were replated at approximately $10^5$ cell/well in 24-well trays and selection reapplied at concentrations up to 100 μM. In both cases there was considerable cell survival at 100 μM. 100 μM MSX-resistant cell pools were expanded in culture and total genomic DNA prepared from initial transfectants and from cell pools resistant to 100 μM MSX.

DNA samples were digested with BglI and BglII restriction enzymes and a Southern blot of the DNA samples was probed with the 0.5 kb 5' PstI GS-cDNA fragment from pGSC45 [7]. The Southern blot analysis is shown in FIG. 3. The DNA probe cross-hybridises with the endogenous mouse GS-gene in NSO cells and this is seen as a fragment of approximately 2.8 kb and one of approximately 6 kb in all transfected cell lines, as well as in non-transfected NSO control DNA. These bands serve as an internal control for loading of the same amount of DNA in each track on the gel. In cells transfected with pSV2BamGS, a 1.2 kb BglII fragment is also detected, which is of the size predicted for vector DNA (from a BglI site in the SV40 promoter to the BglII site at the 3' end of the GS cDNA). By comparison with known amounts of vector DNA loaded in adjacent tracks, the average vector copy number in the SV2GSNSO pool is estimated to be approximately 1 copy/cell. After selection in 100 $\mu$M MSX, the copy number is increased to an average of about 5 copies/cell.

Similarly, introduction of pGMGS into NSO cells has led to the appearance of the predicted 2.1 kb vector fragment in the Southern blot of CMGSNSO DNA at an average level of approximately 1 copy/cell. Selection with 100 $\mu$M MSX has led to an increase in copy-number to approximately 10 copies/cell.

This experiment clearly indicates that pCMGS and pSV2BamGS introduced into NSO cells can be amplified by selection with MSX. No amplification of the endogenous mouse GS genes could be detected.

EXAMPLE 3

In order to test the efficacy of the MSX selection procedure described in Example 1 for the overproduction of recombinant product, the expression of B72.3 cL-chain introduced into NSO cells using GS selection was measured before and after selection with MSX. The transfection frequency was approximately $2 \times 10^{-5}$ colonies/cell transfected for pSV2GScLc and approximately $10^{-3}$ for pCMG-ScLc.

Two NSO-derived cell lines transfected with pSV2GScLc and two cell lines transfected into pCMGScLc, all secreting high levels of cL chain were first recloned by limiting dilution. The expression of cL chain from the 4 highest producing independent clones isolated were estimated by ELISA in comparison with a purified standard preparation of B72.3 cL-chain which had been quantitated by optical density ($OD_{280}$) measurement. The results are shown in Table 7, together with the production rates of MSX-resistant pools derived from these cloned cell lines as described in Example 1. Pools of resistant colonies were isolated at 40 $\mu$M MSX for three of the cell lines and at 100 $\mu$M MSX for cell line C2-27.

TABLE 7

Rates of secretion of cL-chain of B72.3 from transfected NSO cell lines before and after selection for GS-gene amplification.

| | SECRETION RATES (pg/cell/day) | | |
|---|---|---|---|
| CELL LINE | TRANS-FECTANT | AMPLIFIED POOL | AMPLIFIED CLONE |
| SVGScLc-B4.24 | 4.6 | 13 | 20 |
| -C2.27 | 0.4 | 3 | |
| CMGS.cLc-9/6 | 1.5 | 0.2 | |
| -13/7 | 3 | 9 | |

Thus significant increases in productivity are seen for 3 out of the 4 cell lines as a result of selection for resistance to MSX.

The cell-pool with the highest average secretion rate, B4.24 (40 $\mu$M) was cloned by limiting dilution and a clonal cell line was isolated which secreted cL chain at a rate of 20 pg/cell/day. This represents an increase of greater than 4-fold relative to the expression level of the original transfected clone, indicating that selection for GS gene amplification does indeed lead to improved production of the desired recombinant product.

EXAMPLE 4

NSO cells were transfected with a GS-vector containing genes for both the cH and cL chains of the B72.3 antibody in order to express a complete immunoglobulin molecule from a myeloma cell line.

Plasmid pST-6 contains the cH and cL chain cDNA coding sequences, each under the control of an hCMV promoter and a SV40 poly A signal and the SV40 early-GS transcription unit from pSV2BamGS. This plasmid was linearised with SalI and introduced into NSO cells by electroporation as described above. The transfection frequency was approximately $2 \times 10^{-5}$ colonies/cell transfected. Transfectant lines were screened for secretion of functional antibody in a binding assay using antigen-coated plastic plates.

The amount of antibody secreted was then quantitated by an ELISA designed to detect only assembled immunoglobulin. The rates of secretion of assembled antibody for the three of the highest expressing cloned cell lines and MSX-resistant pools derived from them are shown in Table 8.

TABLE 8

| | SECRETION RATES (pg/cell/day) | | MSX* Conc. |
|---|---|---|---|
| CELL LINE | TRANSFECTANT | AMPLIFIED POOL | ($\mu$M) |
| 6A1 | 1.5 | 3.2 | 100 |
| 6-11D3 | 1.2 | 0.6 | 80 |
| 6-11D5 | 0.4 | 0 | 80 |

*MSX concentration is the concentration to which the amplified pools are resistant.

Thus in one of the three cell lines analysed, the expression of antibody is increased significantly by selection for GS-gene amplification. The results in Table 8 obtained using the plasmid pST-6 are markedly different from those obtained using pAb2GS described in Example 1, in which the frequency with which transfectant colonies can be isolated is markedly reduced due to promoter interference. In transfection with pAb2GS, only those few colonies in which the immunoglobulin genes upstream of the GS-gene are exceptionally poorly expressed yield sufficient GS for survival. Consequently the transfectants isolated were poor antibody producers. Using pST-6, it is possible to isolate cell lines secreting much higher levels of antibody. It will be apparent to those skilled in the art that additional alterations to the arrangement of genes on the vector will further reduce transcriptional interference with further beneficial effects of antibody-expression.

EXAMPLE 5 pEE690KGS was the introduced into the myeloma cell line NSO by electroporation as described in Example 1. Transfectants were selected by growth on glutamine free medium (G-DMEM) after plating out in a 96 well plate. The transfection efficiency was approximately 1 in $10^5$ cells transfected.

Wells of the cell culture trays containing single colonies were analysed for secretion of the 90 kD fibrinolytic enzyme by fibrin agar plate assay [8]. Of 33 wells assayed, 26 were clearly positive for fibrinolytic activity. Positive transfectants were then expanded in culture for analysis of the rate of product secretion.

Cell lines isolated in this way secreted between 0.02 and 3.75 pg/cell/day as estimated by fibrin plate assay in comparison with a tissue plasminogen activator (tPA) standard. The 6 cell lines with the highest secretion rates are shown in Table 9. The fibrinolytic activity was shown to have the expected molecular weight of 90 kD by zymography, carried out according to Dodd [9].

The five cell lines with the highest secretion rates were then selected for GS gene amplification using MSX applied in the range 20–80 $\mu$M, as described in Example 2. The specific production rates of MSX resistant cell-pools were determined using the fibrin plate assay and the results are shown in Table 10.

TABLE 9

Production rates of initial transfectant cell lines secreting a 90 kD fibrinolytic enzyme.

| Line | pg/cell/day |
| --- | --- |
| 1 | 3.5 |
| 5 | 0.75 |
| 9 | 1.4 |
| 12 | 1.5 |
| 22 | 1.7 |

TABLE 10

Production rates of cell lines secreting 90 kD fibrinolytic enzyme after one round of selection for vector amplification

| | | Secretion rates | |
| --- | --- | --- | --- |
| Line | MSX Conc | Pool pg/cell/day | Clone pg/cell/day |
| 1 | 40 $\mu$M | 5.8 | 4.5 |
| 5 | 60 $\mu$M | 1.2 | |
| 9 | 80 $\mu$M | 4 | 10.5 |
| 12 | 80 $\mu$M | 5.65 | |
| 22 | 40 $\mu$M | 4.75 | 6 |
| 23 | 60 $\mu$M | 7.5 | |

A second round of selection for vector amplification was then carried out by further increasing the MSX concentration using the first round amplified pools as described in Example 2. Again specific production rates were determined and are shown in Table 11. This second round of selection led to further increases in productivity in each of the pooled cell lines tested, although when clones from these lines were analysed, the highest producers secreted approximately 10 pg/cell/day whether the clones were isolated after the first or the second round of selection for GS amplification. This may indicate that this level of product secretion is saturating for these cell lines.

These results indicate that the level of expression is increased by selection of MSX resistant variants. A clone of line 9 selected for resistance to 80 $\mu$M MSX has a secretion rate increased from 1.4 pg/cell/day to 10.5 pg/cell/day after selection for GS gene amplification, an increase of 7.5 fold.

TABLE 11

Specific Production Rate for 2nd Round Amplified Lines

| Line | [MSX] | Pool pg/cell/day | Clone pg/cell/day |
| --- | --- | --- | --- |
| $1^{40}$ | 100 $\mu$M | 7.75 | |
| $9^{90}$ | 300 $\mu$M | 6.5 | |
| $12^{80}$ | 400 $\mu$M | 7.2 | 10 |
| $22^{40}$ | 300 $\mu$M | 6.4 | 8 |
| $23^{60}$ | 200 $\mu$M | 8.0 | |

It will be appreciated that the present invention has been described above by way of illustration only and that modifications in detail can be made using the skilled person's ordinary knowledge of the art without departing from the scope of the present invention.

REFERENCES

1. Boshart, M., Weber, F., Gerhard, J., Dorsch-Hasler, K., Fleckenstein, B. and Schaffner, W., Cell, 41, 521–530, 1985.
2. Emtage, J. S., Angal, S., Doel, M. T., Harris, T. J. R., Jenkins, B., Lilley, G. and Lowe, P. A., PNAS-USA, 8, 3671–3675, 1983.
3. Mulligan, R. C. and Berg, P., PNAS-USA, 78, 2072–2076, 1981.
4. Melton, D. A., Krieg, P. A., Rebagliati, M. R., Maniatis, T., Zinn, K. and Green, M. R., Nuc. Acid Res., 12, 7035, 1984.
5. Soberon, X., Covarrubias, L. and Bolivar, F., Gene, 9, 287–305, 1980.
6. Whittle, N., Adair, J., Lloyd, C., Jenkins, L., Devine, J., Schlom, J., Raubitschek, A., Colcher, D. and Bodmer, M., Protein Engineering, 1, 499–505, 1987.
7. Hayward, B. E., Hussain, A., Wilson, R. H., Lyons, A., Woodcock, V., McIntosh, B. and Harris, T. J. R., Nuc. Acids Res., 14, 999–1008, 1986.
8. Bishop, R., Ebert, H., Gilchrist, G., Shanbron, E. and Fekete, L., Thrombos. Diathes. Haemorrhagica, 23, 202–210, 1970.
9. Dodd, I., Frars, R. and Robinson, J. H., Thromb. Haemostas. 55, 94–97, 1986.

We claim:

1. A method for preparing a glutamine independent transformed myeloma (lymphoid) cell line which comprises:
   (a) co-transforming a myeloma (lymphoid) cell line with a vector comprising a glutamine synthetase (GS) gene and a vector comprising a gene encoding a protein heterologous to said myeloma (lymphoid) cell line;
   (b) growing said transformed cell line on a medium containing glutamine;
   (c) continuing the growth of said transformed cell line on a selection medium comprising glutamine and asparagine or an ammonia donor and progressively depleting said glutamine from said selection medium; and
   (d) selecting for a glutamine independent transformed myeloma (lymphoid) cell line.

2. The method of claim 1, wherein said vector further comprises a gene encoding a selectable marker other than said GS gene.

3. The method of claim 1, wherein said myeloma (lymphoid) cell line is further co-transformed with a vector comprising a selectable marker other than said GS gene.

4. The method of claim 2, wherein said selectable marker is a gpt gene.

5. The method of claim 3, wherein said selectable marker is a gpt gene.

6. The method of claim 1, wherein said glutamine in said selection medium is progressively depleted by dilution with a medium comprising asparagine and lacking glutamine.

7. The method of claim 1, wherein said protein heterologous to said myeloma (lymphoid) cell line is an immunoglobulin heavy or light chain.

8. The method of claim 1, wherein said GS gene comprises a relatively weak promoter and said gene encoding protein heterologous to said myeloma (lymphoid) cell line comprises a relatively strong promoter, whereby protein synthesis is directed preferentially to the production of the heterologous protein rather than to the production of GS in said transformed myeloma (lymphoid) cell line.

9. A method for preparing a glutamine independent transformed myeloma (lymphoid) cell line which comprises:
   (a) co-transforming a myeloma (lymphoid) cell line with a vector comprising a glutamine synthetase (GS) gene and a vector comprising a gene encoding a protein heterologous to said myeloma (lymphoid) cell line;
   (b) growing said transformed cell line on a medium containing glutamine;
   (c) continuing the growth of said transformed cell line on a glutamine-free selection medium comprising asparagine or an ammonia donor; and
   (d) selecting for a glutamine independent transformed myeloma (lymphoid) cell line.

* * * * *

UNITED STATES PATENT AND TRADEMARK OFFICE
CERTIFICATE OF CORRECTION

PATENT NO. : 5,879,936
DATED : March 9, 1999
INVENTOR(S) : Christopher Robert BEBBINGTON and Geoffrey Thomas YARRANTON It is certified that error appears in the above-identified patent and that said Letters Patent is hereby corrected as shown below:

On the title page item [73],

Change "Aluguisse Holding A.G." to -- Alusuisse Holding A.G. --

Signed and Sealed this

Twenty-first Day of December, 1999

Attest:

Q. TODD DICKINSON

Attesting Officer

Acting Commissioner of Patents and Trademarks